(12) United States Patent
Smith

(10) Patent No.: US 10,226,513 B2
(45) Date of Patent: Mar. 12, 2019

(54) METHOD AND COMPOSITION TO PREVENT OR IMPROVE SYMPTOMS OF MUSCULOSKELETAL DISTRESS DEGENERATION

(71) Applicant: Mark Terrell Smith, Lafayette, CA (US)

(72) Inventor: Mark Terrell Smith, Lafayette, CA (US)

( * ) Notice: Subject to any disclaimer, the term of this patent is extended or adjusted under 35 U.S.C. 154(b) by 0 days.

(21) Appl. No.: 14/990,248

(22) Filed: Jan. 7, 2016

(65) Prior Publication Data

US 2016/0199456 A1    Jul. 14, 2016

Related U.S. Application Data

(60) Provisional application No. 62/101,893, filed on Jan. 9, 2015.

(51) Int. Cl.
| | | |
|---|---|---|
| *C07K 14/00* | (2006.01) | |
| *A61K 38/39* | (2006.01) | |
| *A61K 45/06* | (2006.01) | |
| *A61K 33/06* | (2006.01) | |
| *A61K 33/26* | (2006.01) | |
| *A61K 33/30* | (2006.01) | |

(52) U.S. Cl.
CPC .............. *A61K 38/39* (2013.01); *A61K 33/06* (2013.01); *A61K 33/26* (2013.01); *A61K 33/30* (2013.01); *A61K 45/06* (2013.01); *C07K 14/00* (2013.01)

(58) Field of Classification Search
None
See application file for complete search history.

(56) References Cited

U.S. PATENT DOCUMENTS

| | | | | |
|---|---|---|---|---|
| 4,379,143 A | * | 4/1983 | Sherry | A61K 8/02 424/684 |
| 5,399,347 A | | 3/1995 | Trentham et al. | |
| 5,637,321 A | * | 6/1997 | Moore | A61K 35/32 424/464 |
| 5,783,188 A | | 7/1998 | Weiner et al. | |
| 6,083,918 A | | 7/2000 | Klaus | |
| 6,162,787 A | | 12/2000 | Sorgente et al. | |
| 6,224,871 B1 | | 5/2001 | Hastings et al. | |
| 6,323,319 B1 | | 11/2001 | Aikayali | |
| 7,083,820 B2 | | 8/2006 | Schilling et al. | |
| 7,083,829 B2 | | 8/2006 | Hoke et al. | |
| 7,495,076 B2 | | 2/2009 | Gu et al. | |
| 7,608,588 B2 | | 10/2009 | Gu et al. | |
| 7,718,366 B2 | | 5/2010 | Tsai et al. | |
| 7,759,310 B2 | | 7/2010 | Gu et al. | |
| 7,846,487 B2 | | 12/2010 | Schilling et al. | |
| 8,344,106 B1 | | 1/2013 | Summers et al. | |
| 8,563,045 B2 | | 10/2013 | Ishaq | |
| 8,778,422 B2 | | 7/2014 | Oesser | |
| 9,066,926 B2 | | 6/2015 | Dijkstra et al. | |
| 9,072,799 B2 | | 7/2015 | Boyden et al. | |
| 2011/0262552 A1 | * | 10/2011 | Chamberland | A61K 36/185 424/547 |
| 2015/0119335 A1 | | 4/2015 | Dijkstra et al. | |

* cited by examiner

*Primary Examiner* — Lianko G Garyu

(57) ABSTRACT

The present invention relates generally to compositions and methods of using compositions comprised of undenatured cartilage in the form of an isolated native Type II collagen that may be combined in a synergistic blend with one or more edible metals with acceptable chemical counter-ions or other health promoting ingredients to be orally consumed as a method for preventing and improving symptoms of musculoskeletal distress degeneration, including symptoms selected from temporary loss of range of motion, temporary inflammation, temporary muscle soreness, and combinations thereof. The synergistic compositions of the present invention also protect, promote and improve recovery from and prevention of cartilage and ligament wear, thinning and damage to bone, and repetitive motion injuries and stress resulting from intense periods of activity or workout routines that contribute to such musculoskeletal distress degeneration symptoms.

7 Claims, No Drawings

Specification includes a Sequence Listing.

METHOD AND COMPOSITION TO PREVENT OR IMPROVE SYMPTOMS OF MUSCULOSKELETAL DISTRESS DEGENERATION

RELATED APPLICATIONS

This present application claims the priority of U.S. Provisional Patent Application No. 62/101,893 (filed on Jan. 9, 2015) which is incorporated herein by reference in its entirety.

FIELD OF THE INVENTION

The present invention relates generally to a composition comprised of ground cartilage and optionally one mineral metal with an acceptable chemical counter-ion to be orally consumed as a method to preventing or improving symptoms of musculoskeletal distress degeneration. More specifically, the present invention relates to a therapeutic composition comprised of a synergistic blend of type II collagen, and at least one metal salt selected from the disclosed list mentioned herein below.

BACKGROUND OF THE INVENTION

The invention further relates to a method to use the described composition to:
 (i) reduce or remove existing symptoms or prevent the user from incurring symptoms resulting from musculoskeletal distress such as a measurable decrease in the range of movement, a measurable increase in muscle soreness, or a measurable amount of inflammation resulting from physical exertion, and/or
 (ii) to reduce or prevent longer-term detrimental effects associated with such physical activities, such as bone, cartilage or ligament wear, thinning or damage, and/or
 (iii) to help maintain any metabolic metal mineral or electrolyte imbalances or depletion resulting from metabolic processes induced by such activities (e.g. osteopenia) by delivering the composition using an acceptable carrier for an acceptable period of time.

The core components of the invention are comprised of a blend of at least 0.1% by weight of type II collagen derived from an acceptable source, and at least 0.1% by weight of one acceptable edible metal salt selected from the group Magnesium (Mg), Manganese (Mn), Calcium (Ca), Zinc (Zn) or Iron (Fe), where all metal ions are bound or associated to a counter-ion appropriate for the intended use, and which, generally speaking, are blended into an acceptable carrier or delivery mechanism for the intended use.

Furthermore, with respect to the composition, it should be noted that:
 (i) the type II collagen is most likely (>98% amino acid match according to known databases) coded by the COL2A1 gene and derived from an avian or mammalian source,
 (ii) is not-likely hydrolyzed or enzymatically cleaved,
 (iii) the type II collagen may or may not be in its native state and may or may not require stabilization by preservatives or other additives.

With respect to the associated method, generally speaking, it is anticipated that the composition is orally administered using an acceptable delivery vehicle and for a period of at least 7 days and up to a maximum of 20 years. Furthermore, it should be further noted that the invention may be used by humans or animals, pets, or other individuals who present symptoms of musculoskeletal distress including pain, stiffness, fatigue, weakness, limited range of movement, or inflammation, the composition may simultaneously be used to prevent the long-term degradation or weakening of the bone and its constituent fibers and inorganic materials.

Individuals who, due to a variety of factors including age, injury, repetitive stress, regular exercise, physical activity or bearing heavy loads, frequently experience short term side effects that include temporary loss of range of motion, inflammation, or muscle soreness. These conditions, which may lead to long term effects such as bone wear, weakened tendons or other chronic issues. In most cases, such symptoms do not require clinical treatment and a medical prescription, is not necessary, however, they do interfere with regular activities such as work, exercise and child-care. Existing commercial oral remedies often require multi-gram doses, and have low compliance and/or low response rates. It would be desirable to have a composition that can be delivered in a small and effective daily dose, preferably less than 1 grain per serving per day, and even more preferably less than 100 milligrams per day, which/that can reduce or prevent or remove both measurable short term symptoms of distress and/or chronic long-term and measurable health symptoms associated with musculoskeletal wear and metabolic imbalances resulting from high physical activity levels, physical exertion, sports, or repetitive motions.

Furthermore, it would also be desirable to have a composition that uses safe and effective ingredients that do not require oversight by a physician. Still further, it would be desirable to have a composition that may be administered orally without sophisticated medical technology, and would be effective by more than one mechanism of action so as to increase the percentage of the population for which it is effective. Therefore, there currently exists a need in the industry for a composition and/or an associated method to counteract symptoms of musculoskeletal distress in the broad population and slow degenerative processes by administering a small effective dose of a composition comprised by type II collagen, and at least one acceptable metal salt selected from the group of Magnesium (Mg), Manganese (Mn), Calcium (Ca), Iron (Fe), and/or Zinc (Zn), where metals are bound or associated with an acceptable counter-ion or carrier.

The present invention is unique in that it is different from other dietary supplement compositions, and is administered in a dose of not more than 1000 mg.

More specifically, the present invention is unique due to the presence of the combination of:
 (1) a type II collagen protein that is not enzymatically hydrolyzed,
 (2) at least one salt of a mineral selected from the group calcium, magnesium, zinc, iron, and manganese, and optionally
 (3) other additives including but not limited to Vitamin classes A, B, D, E and K, amino acids or hyaluronic acid. Furthermore, the process associated with the aforementioned invention is likewise unique and different from known processes and solutions.

More specifically, the present invention process owes its uniqueness to the fact that the small effective oral dose may be attributed to the dual action of the immune response, bone resorption and tissue repairing and maintenance effects of the composition.

SUMMARY OF THE INVENTION

The present invention generally relates to a method of treating musculoskeletal distress in healthy active humans and animals comprising administering an undenatured Type II collagen in an effective amount sufficient to reduce at least one symptom resulting from said musculoskeletal distress; wherein said symptom is selected from temporary loss of range of motion, temporary inflammation, temporary muscle soreness, and combinations thereof.

The present invention further relates generally to a method of treating the symptoms of musculoskeletal distress and simultaneously providing one additional health benefit comprising administering (a) an undenatured Type II collagen; and (b) at least one soluble, edible metal salt; wherein said collagen is administered at an effective amount sufficient to reduce at least one symptom resulting from said musculoskeletal distress; and wherein said metal salt is administered at an effective amount sufficient to provide said additional health benefit; wherein said additional health benefit is selected from bone resorption, tissue reparation, prevention of detrimental effects on bone, cartilage and ligament, and prevention of metal imbalances resulting from metabolic processes induced by said musculoskeletal distress.

The present invention also further relates generally to compositions and methods of using said compositions for treating the symptoms of musculoskeletal distress and simultaneously providing at least one additional health benefit comprising: (a) undenatured Type II collagen; (b) at least one edible metal salt selected from magnesium, manganese, calcium, zinc and iron; (c) at least one amino acid selected from L-glutamine, L-Leucine, branched amino acids, and combinations thereof; and (d) optionally, a vitamin selected from Vitamin A, B, D, E, K and combinations thereof; wherein said additional health benefit is selected from bone resorption and tissue reparation.

DETAILED DESCRIPTION OF THE INVENTION

All illustrations of the drawings are for the purpose of describing selected versions of the present invention and are not intended to limit the scope of the present invention.

In its most complete form, the present invention composition is comprised of the following components: 0.1% to 95% by weight of Type II collagen derived from an acceptable source and 5%-99.9% of a mineral or blend of minerals, and 0-99.5% an amino acid selected from glutamine, a branched chain amino acid, or a vitamin selected from the groups Vitamin B, D, E and K, and which preferably weighs less than 1000 milligrams per serving in its embodiment.

These components are to be blended and mixed into an acceptable delivery medium such as a capsule, tablet or flavored delivery system for oral consumption. It should further be noted that: An acceptable type II collagen source is most likely not been enzymatically processed or hydrolyzed in order to maintain the integrity of the native state of the collagen; the acceptable type of collagen may be identified by a greater than a 98% match of the following amino acid sequence (SEQ ID No:1) according to a BLAST protein identification search and identified herein as Seq. ID. No. 1.:

SPPCACHICKCLLAGENALPHAIICHAINFRAGMENTSGALLSGALLSGN

CLAPESVGETGEAGERGLKGHRGFTGLQGLPGPPGPSGDQGAAGPAGPSG

PRGPPGPVGPSGKDGSNGMPGPIGPPGPRGRSGEPGPAGPPGNPGPPGPP

GPPGTGIDMSAFAGLGQTEKGPDPIRYMRADEAAGGLRQHDVEVDATLKS

-continued

LNNQIESIRSPEGSKKNPARTCRDIKLCHPEWKSGDYWIDPNQGCTLDAI

KVFCNMETGETCVYPTPSSIPRKNWWTSKTKDKKHVWFAETINGGFHFSY

GDENLSPNTASIQMTFLRLLSTEGSQNVTYHCKNSIAYMDEETGNLKKAI

LIQGSNDVEIRAEGNSRFTYSVLEDGCTKHTGKWGKTVIEYRSQKTSRLP

IVDIAPMDIGGADQEFG VDIGPVCFL

Seven prophetic examples of the invention are given below. The intended to be homogeneously blended so as to be ready for encapsulation, tableting or further processing so they may be orally consumed using in an acceptable form.

A first prophetic example of an embodiment of the invention is: 40 milligrams of type II collagen 200 milligrams of calcium citrate.

A second example of an embodiment of the invention is: 40 milligrams of type II collagen 65 milligrams of a magnesium oxide 200 milligrams of calcium citrate.

A third example of an embodiment of the invention is: 40 milligrams of type II collagen 65 milligrams of a magnesium chloride 600 milligrams of calcium citrate 100 milligrams of L-glutamine.

A fourth example of an embodiment of the invention is: 300 milligrams of type II collagen 60 milligrams of a zinc oxide 600 milligrams of calcium EDTS 200 milligrams of L-leucine.

A fifth example of an embodiment of the invention is: 40 milligrams of type II collagen 65 milligrams of a magnesium oxide 600 milligrams of calcium EDTS 200 milligrams of L-leucine.

A sixth example of an embodiment of the invention is 40 milligrams of type 11 collagen 500 milligrams of hyaluronic acid 65 milligrams of magnesium chloride.

A seventh example of an embodiment of the invention is 20 milligrams of type II collagen 10 milligrams of magnesium sulphate.

The most complete form of performing the method associated with the present invention device consists of the following steps:
1. Blending the components of the composition if it has not already been done;
2. Encapsulating, tableting or inserting the composition into another delivery formula such as a gummy or drinkable formula;
3. Delivering the composition to an animal or human with the described musculoskeletal disorder, or who desires to benefit from the preventative or other health effects of consuming the composition.

It should further be noted that: a desirable period for consuming this composition is between 7 days and 20 years. The present invention is distinct from previous inventions in the following ways:

The present composition and method of treatment is not initially designed to treat a disease, but as a nutritional supplement or other edible composition to be added to food to aid in the recovery from or prevention of exercise or repetitive motions and maintain the health of athletically or overly physically active individuals from the effects of over-use or over-loading their musculoskeletal system during; for instance existing inventions describe collagen and glucosamine and chondroitin based treatments for rheumatoid, osteoarthritic, multiple sclerosis and related "defective" conditions.

It is non-obvious that previously disclosed disease treatments would be effective for temporary musculoskeletal distress the composition and method jointly provide a previously undisclosed "dual action" musculoskeletal preservation and restoration system whereby both autoimmune function (via T cell regulation) is induced using native and insoluble type II collagen, and simultaneously bone resorption and tissue reparation effects of the metal salts and/or vitamins and amino acids. Such an approach has not been previously been reported to the author's knowledge at the time of writing in contrast to the present invention, related dietary supplements often intentionally hydrolyze the type II collagen (for examples, existing inventions disclose where the collagen is hydrolyzed) or otherwise alter the collagen protein (through another existing invention: the collagen is hydrolyzed and then used to bind calcium, which further alters the protein structure); using a type II collagen source that is not-hydrolyzed and retains its native structure is essential to the present invention and is responsible for the unique mechanisms by which it is effective; the method of obtaining a type II collagen of at least 50 KD and from an acceptable source is not obvious, as this protein is difficult to extract from appropriate sources.

Functional Uses of the Invention

The present invention is unique when compared with many dietary supplement compositions because the present invention provides:

(1) In one example embodiment, a very small and effective dose of under 50 milligrams per serving per day, and a maximum of 1000 milligrams per serving. By contrast examples of hydrolyzed collagen report 500 milligrams in existing inventions for soluble hydrolyzed collagen, or 250 milligrams for glucosamine sulphate. (These inventions have different uses than the composition reported here and are only used to illustrate quantitative differences).

Commercial materials have traditionally used doses of over 1500 milligrams per day, obtaining treatments with a high impact at doses lower than those previously used are not obvious.

(2) In another example embodiment, the invention is a unique method for maintaining or improving healthy musculoskeletal function for healthy active humans and animals during intense periods of activity distress or workout routines and;

(3) In yet another example embodiment, compositions of the invention act by a dual mechanism of action that is distinct from traditional dietary supplements for bone or joint troubles.

In one embodiment, the present invention is a composition to be consumed orally as a dietary supplement or other edible composition for reducing or removing musculoskeletal distress and building healthy musculoskeletal function and mobility range. The composition is comprised of type II collagen derived from an acceptable source, and at least one mineral selected from the group previously listed. In another embodiment, the invention is a method for maintaining healthy musculoskeletal function for healthy individuals who are periodically or constantly excessively physically active, bear heavy weight loads for short or long periods of time or perform repetitive motions that may cause measurable symptoms. The method involves delivering a daily dose of the described composition for a period of at least 7 days, and up to 20 years to an otherwise healthy human or animal.

Additional Optional Additives for the Present Invention

The invention may further be combined with other vitamins or amino acids, including, but not limited to vitamins A, B, D, E or K, L-glutamine, or other branched chain amino acids, such as L-Leucine, hyaluronic acid, or additives in order to increase the musculoskeletal benefits of the formula. The final weight of the composition may vary between 20-2000 milligrams, depending on the appropriate application and individual or animal. Concerning the method, the method may further include the treatment or prevention of the symptoms associated with bone aging and wear, such as Osteopenia, or optional arthritic symptoms that do not require application by a physician. The method may also be used in animals such as dogs, cats, horses, or other domestic or animals that bare heavy loads, are athletically inclined, or have musculoskeletal distress induced by activities or may be disposed to do so and wish to prevent such symptoms. In another form, the method may also require the use of a new carrier, such as a gummy, or other delivery system that improves the efficacy or likelihood of compliance with the method described.

Although the invention has been explained in relation to its preferred embodiment, it is to be understood that many other possible modifications and variations can be made without departing from the spirit and scope of the invention.

What is claimed is:

1. A composition for treating the symptoms of musculoskeletal distress and simultaneously providing at least one additional health benefit comprising: (a) undenatured Type II collagen; (b) at least one edible metal salt selected from magnesium, manganese, calcium, zinc and iron; (c) at least one amino acid selected from L-glutamine, L-Leucine, branched amino acids, and combinations thereof; and (d) optionally, a vitamin selected from Vitamin A B, D, E, K and combinations thereof; wherein said additional health benefit is selected from bone resorption and tissue reparation and wherein said undenatured Type II collagen comprises greater than 98% sequence identity to the amino acid sequence of SEQ ID NO: 1.

2. The composition of claim 1 further comprising at least two edible metal salts selected from magnesium, manganese, calcium, zinc, iron and combinations thereof.

3. The composition of claim 1 wherein said undenatured Type II collagen consists of the amino acid sequence set out in SEQ ID NO: 1.

4. A method of treating the symptoms of musculoskeletal distress and simultaneously providing one additional health benefit comprising administering (a) an undenatured Type II collagen according to claim 1; and (b) at least one soluble, edible metal salt; wherein said collagen is administered at an effective amount sufficient to reduce at least one symptom resulting from said musculoskeletal distress; and wherein said metal salt is administered at an effective amount sufficient to provide said additional health benefit; and wherein said additional health benefit is selected from bone resorption and tissue reparation.

5. The method of claim 4 wherein said metal salt is selected from magnesium, manganese, calcium, zinc, iron and combinations thereof.

6. The method of claim 4 wherein said metal salt is magnesium and a second soluble, edible metal salt is selected from calcium, manganese, zinc and iron.

7. The method of claim 4 wherein said undenatured Type II collagen consists of the amino acid sequence set out in SEQ ID NO: 1.

* * * * *

SEQUENCE LISTING

```
<160> NUMBER OF SEQ ID NOS: 1

<210> SEQ ID NO 1
<211> LENGTH: 426
<212> TYPE: PRT
<213> ORGANISM: Chicken
<220> FEATURE:
<221> NAME/KEY: Chain
<222> LOCATION: (1)..(123)
<220> FEATURE:
<221> NAME/KEY: ProPeptide
<222> LOCATION: (124)..(369)
<300> PUBLICATION INFORMATION:
<308> DATABASE ACCESSION NUMBER: Uniprot/P02460
<309> DATABASE ENTRY DATE: 1986-07-21
<313> RELEVANT RESIDUES IN SEQ ID NO: (1)..(369)

<400> SEQUENCE: 1

Ser Pro Pro Cys Ala Cys His Ile Cys Lys Cys Leu Leu Ala Gly Glu
1               5                   10                  15
```

```
Asn Ala Leu Pro His Ala Ile Ile Cys His Ala Ile Asn Phe Arg Ala
             20                  25                  30

Gly Met Glu Asn Thr Ser Gly Ala Leu Leu Ser Gly Ala Leu Leu Ser
         35                  40                  45

Gly Asn Cys Leu Ala Pro Glu Ser Val Gly Glu Thr Gly Glu Ala Gly
 50                  55                  60

Glu Arg Gly Leu Lys Gly His Arg Gly Phe Thr Gly Leu Gln Gly Leu
 65                  70                  75                  80

Pro Gly Pro Pro Gly Pro Ser Gly Asp Gln Gly Ala Ala Gly Pro Ala
                 85                  90                  95

Gly Pro Ser Gly Pro Arg Gly Pro Pro Gly Pro Val Gly Pro Ser Gly
             100                 105                 110

Lys Asp Gly Ser Asn Gly Met Pro Gly Pro Ile Gly Pro Pro Gly Pro
             115                 120                 125

Arg Gly Arg Ser Gly Glu Pro Gly Pro Ala Gly Pro Pro Gly Asn Pro
 130                 135                 140

Gly Pro Pro Gly Pro Pro Gly Pro Pro Gly Thr Gly Ile Asp Met Ser
145                 150                 155                 160

Ala Phe Ala Gly Leu Gly Gln Thr Glu Lys Gly Pro Asp Pro Ile Arg
                 165                 170                 175

Tyr Met Arg Ala Asp Glu Ala Ala Gly Gly Leu Arg Gln His Asp Val
             180                 185                 190

Glu Val Asp Ala Thr Leu Lys Ser Leu Asn Asn Gln Ile Glu Ser Ile
             195                 200                 205

Arg Ser Pro Glu Gly Ser Lys Lys Asn Pro Ala Arg Thr Cys Arg Asp
 210                 215                 220

Ile Lys Leu Cys His Pro Glu Trp Lys Ser Gly Asp Tyr Trp Ile Asp
225                 230                 235                 240

Pro Asn Gln Gly Cys Thr Leu Asp Ala Ile Lys Val Phe Cys Asn Met
                 245                 250                 255

Glu Thr Gly Glu Thr Cys Val Tyr Pro Thr Pro Ser Ser Ile Pro Arg
             260                 265                 270

Lys Asn Trp Trp Thr Ser Lys Thr Lys Asp Lys Lys His Val Trp Phe
             275                 280                 285

Ala Glu Thr Ile Asn Gly Gly Phe His Phe Ser Tyr Gly Asp Glu Asn
             290                 295                 300

Leu Ser Pro Asn Thr Ala Ser Ile Gln Met Thr Phe Leu Arg Leu Leu
305                 310                 315                 320

Ser Thr Glu Gly Ser Gln Asn Val Thr Tyr His Cys Lys Asn Ser Ile
                 325                 330                 335

Ala Tyr Met Asp Glu Glu Thr Gly Asn Leu Lys Lys Ala Ile Leu Ile
             340                 345                 350

Gln Gly Ser Asn Asp Val Glu Ile Arg Ala Glu Gly Asn Ser Arg Phe
             355                 360                 365

Thr Tyr Ser Val Leu Glu Asp Gly Cys Thr Lys His Thr Gly Lys Trp
             370                 375                 380

Gly Lys Thr Val Ile Glu Tyr Arg Ser Gln Lys Thr Ser Arg Leu Pro
385                 390                 395                 400

Ile Val Asp Ile Ala Pro Met Asp Ile Gly Ala Asp Gln Glu Phe
                 405                 410                 415

Gly Val Asp Ile Gly Pro Val Cys Phe Leu
             420                 425
```